United States Patent
Kato et al.

(10) Patent No.: US 10,251,572 B2
(45) Date of Patent: Apr. 9, 2019

(54) PULSE WAVE DETECTION APPARATUS

(71) Applicant: OMRON HEALTHCARE CO., LTD., Muko-shi, Kyoto (JP)

(72) Inventors: Yuki Kato, Kyoto (JP); Masayuki Wakamiya, Kyoto (JP); Toshihiko Ogura, Kyoto (JP)

(73) Assignee: OMRON HEALTHCARE CO., LTD., Muko (JP)

(*) Notice: Subject to any disclaimer, the term of this patent is extended or adjusted under 35 U.S.C. 154(b) by 383 days.

(21) Appl. No.: 15/199,154

(22) Filed: Jun. 30, 2016

(65) Prior Publication Data

US 2016/0310021 A1    Oct. 27, 2016

Related U.S. Application Data

(63) Continuation of application No. PCT/JP2015/051273, filed on Jan. 19, 2015.

(30) Foreign Application Priority Data

Jan. 31, 2014   (JP) ................ 2014-017727

(51) Int. Cl.
   *A61B 5/021*    (2006.01)
   *A61B 5/024*    (2006.01)
   (Continued)

(52) U.S. Cl.
   CPC ........ *A61B 5/0245* (2013.01); *A61B 5/02108* (2013.01); *A61B 5/02444* (2013.01);
   (Continued)

(58) Field of Classification Search
   CPC ... A61B 5/024; A61B 5/0245; A61B 5/02438; A61B 5/02444; A61B 5/021;
   (Continued)

(56) References Cited

U.S. PATENT DOCUMENTS

| | | | |
|---|---|---|---|
| 4,947,855 A | 8/1990 | Yokoe et al. | |
| 5,101,829 A * | 4/1992 | Fujikawa | A61B 5/022 600/485 |

(Continued)

FOREIGN PATENT DOCUMENTS

| | | |
|---|---|---|
| JP | S63-294832 A | 12/1988 |
| JP | 2577984 B2 | 2/1997 |

(Continued)

OTHER PUBLICATIONS

Apr. 7, 2015 International Search Report issued in International Patent Application No. PCT/JP2015/051273.

(Continued)

*Primary Examiner* — Thaddeus B Cox
(74) *Attorney, Agent, or Firm* — Oliff PLC

(57) ABSTRACT

A pulse wave detection apparatus has a sensor chip that includes a substrate that has a shape of extending so as to be elongated in an X direction, and that is arranged so as to intersect an artery. A pressure sensor array is formed on the substrate and is made up of pressure sensor elements that are arranged side-by-side in the X direction. An electrode terminal array for transmitting output from the pressure sensor elements to the outside of the sensor chip is formed in a region that opposes an end portion of the pressure sensor array on the substrate. Regions that correspond to two sides of the pressure sensor array on the substrate are planar surfaces on which electrode terminals are not located.

18 Claims, 15 Drawing Sheets

(51) Int. Cl.
*A61B 5/0245* (2006.01)
*A61B 5/00* (2006.01)
(52) U.S. Cl.
CPC ............ *A61B 5/725* (2013.01); *A61B 5/7225* (2013.01); *A61B 5/7235* (2013.01); *A61B 5/742* (2013.01); *A61B 5/02116* (2013.01); *A61B 5/7203* (2013.01); *A61B 2562/0247* (2013.01); *A61B 2562/043* (2013.01); *A61B 2562/12* (2013.01)
(58) Field of Classification Search
CPC ........ A61B 5/02108; A61B 2562/0247; A61B 2562/043
See application file for complete search history.

(56) References Cited

U.S. PATENT DOCUMENTS

2004/0193061 A1* 9/2004 Sato ..................... A61B 5/02
600/500
2005/0267375 A1* 12/2005 Satoh .................... A61B 5/021
600/500
2009/0321266 A1* 12/2009 Egawa ................... H05K 3/242
205/125
2014/0296687 A1* 10/2014 Irazoqui .................. A61B 3/16
600/398

FOREIGN PATENT DOCUMENTS

| | | |
|---|---|---|
| JP | 2006-020823 A | 1/2006 |
| JP | 2011-239840 A | 12/2011 |
| KR | 2009-0011479 A | 2/2009 |

OTHER PUBLICATIONS

Mar. 21, 2018 Office Action issued in Chinese Patent Application No. 201580003402.X.

* cited by examiner

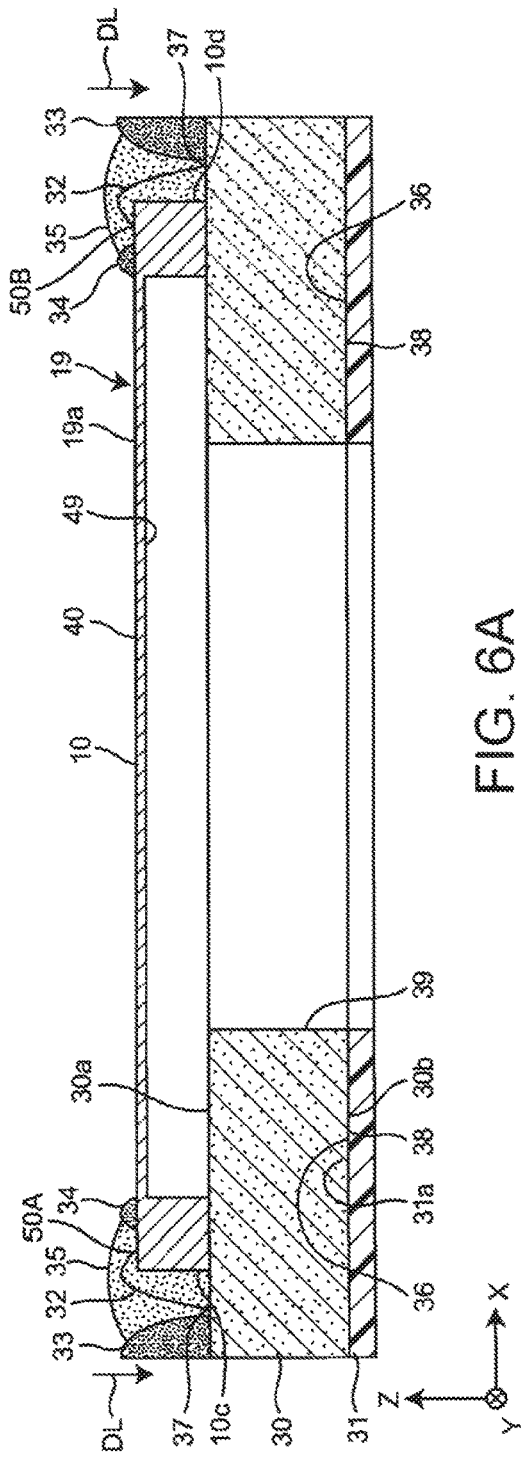
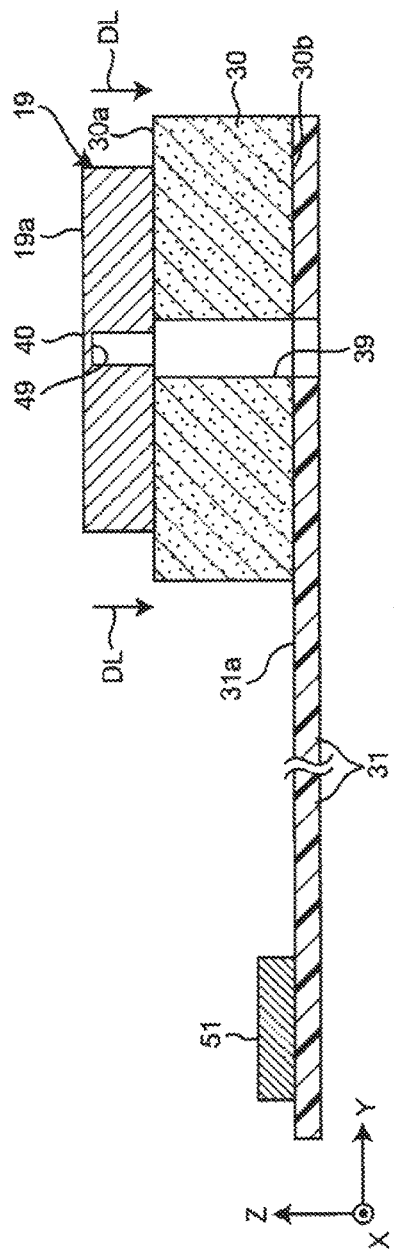
FIG. 6A
FIG. 6B

WAVEFORM

TONOGRAM

PULSE WAVE DETECTION APPARATUS

TECHNICAL FIELD

This invention relates to a pulse wave detection apparatus, and more specifically relates to a pulse wave detection apparatus that detects a pulse wave in a noninvasive manner by pressing a sensor chip, which has a pressure sensor (strain sensor) array formed thereon, against a measurement site through which an artery passes.

BACKGROUND ART

In a known example of this type of pulse wave detection apparatus, a sensor chip, on which a pressure sensor (strain sensor) array has been formed using MEMS (Micro Electro Mechanical Systems) technology, is pressed against a measurement site through which an artery passes, and change in the internal pressure of the artery, that is to say a pulse wave, is measured in a noninvasive manner using tonometry, as disclosed in Patent Literature 1 (JP 2011-239840A) for example.

Among commercial products for measuring blood pressure (including change in the internal pressure of an artery) in a noninvasive manner using tonometry, there are products that include a sensor chip having the pattern layout shown in FIG. 16(A). In this example, the sensor chip 101 includes an approximately flat plate-shaped silicon substrate 102 that is elongated in one direction (X direction), a pressure sensor array 110 formed on the silicon substrate 102 at approximately the center in the Y direction (direction perpendicular to the X direction), and electrode terminal arrays 120A and 120B formed along long sides 102a and 102b on two sides in the Y direction. The pressure sensor array 110 is made up of pressure sensor (strain sensor) elements 11 arranged side-by-side in the X direction with a fixed pitch. The electrode terminal arrays 120A and 120B are each made up of gold bump electrodes 121, 121, . . . arranged side-by-side in the X direction with a fixed pitch. The pressure sensor elements 11l of the pressure sensor array 110 are connected to the corresponding gold bump electrodes 121 of the electrode terminal arrays 120A and 120B via interconnects (not shown) formed on the silicon substrate 102. As shown in FIG. 16(B) (cross-section along line B-B in FIG. 16(A)), the pressure sensor array 110 is formed on a thin region 119 provided by forming a recessed shape in the lower surface side (−Z side) of the silicon substrate 102. The lower surface side of the silicon substrate 102 is supported by a glass plate 103. Through-holes 103A and 103B, which allow the flow of air between the thin region (recessed portion) 119 and the outside, are provided in the glass plate 103 so as to not hinder flexure of the pressure sensor elements 111 in the Z direction.

As shown in FIG. 17, in a product with the sensor chip 101 mounted thereon, flexible wiring boards 130A and 130B are connected to the gold bump electrodes 121, 121 of the electrode terminal arrays 120A and 120B. Processing circuits (not shown) for processing signals from the pressure sensor elements 111 are implemented on the flexible wiring boards 130A and 130B. Also, a protective sheet 140 made of resin is provided so as to cover the entirety of the upper surface of the sensor chip 101.

When performing blood pressure measurement using tonometry, the sensor chip 101 is pressed against a measurement site 90 through which an artery 91 passes, as shown in FIG. 18. Accordingly, the artery 91 is pressed with an external pressure Po via the sensor chip 101, not such that the artery 91 is completely crushed, but rather such that only a portion 91a of the vascular wall of the artery 91 (the portion in the vicinity of a body surface 90a that opposes the sensor chip 101, which is hereinafter called the "outward-facing portion") becomes flattened. In other words, the radius of curvature of the vascular wall of the outward-facing portion 91a is set to infinity. At this time, the sensor chip 101 is arranged such that the lengthwise direction thereof, that is to say the extending direction of the pressure sensor array 110 (X direction), intersects the artery 91. In this arrangement, based on the output of the pressure sensor elements 111, 111, . . . included in the pressure sensor array 110, an appropriate pressure sensor element 111 is selected from the pressure sensor array 110. Change in the internal pressure of the artery 91 is then measured based on the output from the selected pressure sensor element 111.

Specifically, as shown illustratively in FIG. 19(B), while maintaining equilibrium between the external pressure Po and a blood vessel internal pressure Pi, the internal pressure (blood pressure pulse wave) Pi pulsating against the external pressure Po is obtained. Note that as shown illustratively in FIG. 19(A), if a flat portion is not formed in the artery 91, the radius of curvature of the vascular wall (indicated by r) becomes relatively smaller in Po=Pi+T/r, which is the relational expression for the external pressure Po and the internal pressure Pi. For this reason, the external pressure Po and the blood vessel internal pressure Pi substantially do not match, and accurate measurement cannot be performed.

CITATION LIST

Patent Literature

Patent Literature 1: JP 2011-239840A

SUMMARY OF INVENTION

Technical Problem

In conventional commercial products, when a cross-section perpendicular to the extending direction of the pressure sensor array 110 (a cross-section substantially along the artery 91) is viewed as shown in FIG. 17, the flexible wiring boards 130A and 130B connected to the gold bump electrodes 121, 121 are located in the vicinity of the long sides 102a and 102b on the two sides of the sensor chip 101, and therefore portions 140a and 140b of the protective sheet 140 that are in the vicinity of the long sides 102a and 102b on the two sides bulge in a manner of protruding outward (toward the measurement site 90) as shown by arrows E. For this reason, there is a problem in that the protruding bulging portions 140a and 140b are obstacles to flattening the outward-facing portion 91a of the vascular wall of the artery 91. As a result, there is a possibility of not being able to set the radius of curvature to infinity, and being influenced by tensile force from the vascular wall such that the measurement precision decreases.

In view of this, a problem to be solved by this invention is the provision of a pulse wave detection apparatus that detects a pulse wave in a noninvasive manner by pressing a sensor chip, which has a pressure sensor array formed thereon, against a measurement site through which an artery passes, in which the outward-facing portion of the vascular wall of an artery can be flattened with good precision, thus making it possible to accurately obtain the internal pressure of the blood vessel.

Solution to Problem

In order to solve the above-described problem, a pulse wave detection apparatus of this invention is a pulse wave detection apparatus that detects a pulse wave in a noninvasive manner by pressing a sensor chip having a pressure sensor array formed thereon against a measurement site through which an artery passes, the sensor chip including:
- a substrate that has a shape of extending so as to be elongated in one direction, and that is arranged so as to intersect the artery;
- a pressure sensor array that is formed on the substrate and is made up of a plurality of pressure sensor elements arranged side-by-side in the one direction; and
- an electrode terminal array that is made up of a plurality of electrode terminals arranged side-by-side in a direction perpendicular to the one direction, and that is for transmitting output from the plurality of pressure sensor elements to the outside of the sensor chip, the electrode terminal array being formed in a region that opposes an end portion of the pressure sensor array on the substrate, wherein regions that correspond to two sides of the pressure sensor array on the substrate are substantially planar surfaces on which electrode terminals are not located, and a processing circuit that processes output from the pressure sensor elements of the pressure sensor array and transmits the processed output to an electrode terminal of the electrode terminal array is formed in an integrated manner on the substrate.

In this specification, a "substantially planar surface" need only feel planar when the sensor chip is pressed against a measurement site through which an artery passes, and this term has a meaning that permits very small roughness on the order of microns (e.g., level differences of thin films that arise in the semiconductor process for manufacturing the sensor chip).

In the above pulse wave detection apparatus of this invention, at the time of blood pressure measurement, the sensor chip is pressed against a measurement site through which an artery passes. At this time, the lengthwise direction of the sensor chip, that is to say the extending direction of the pressure sensor array, is oriented so as to intersect the artery. Then, based on the output of the pressure sensor elements included in the pressure sensor array, an appropriate pressure sensor element (e.g., the one that output the highest pulse wave signal) is selected from the pressure sensor array. Change in the internal pressure of the artery (i.e., a pulse wave) is then measured based on the output from the selected pressure sensor element.

Here, in this pulse wave detection apparatus, the output of the pressure sensor elements is transmitted to the outside of the sensor chip via an electrode terminal array formed in a region that opposes an end portion of the pressure sensor array on the substrate. Regions that correspond to two sides of the pressure sensor array on the substrate are substantially planar surfaces on which electrode terminals are not located. Accordingly, in a cross-section perpendicular to the extending direction of the pressure sensor array (a cross-section substantially along the artery), there are no obstacles to flattening the outward-facing portion of the vascular wall of the artery. As a result, the outward-facing portion of the vascular wall of the artery can be flattened with good precision. Accordingly, change in the internal pressure of the artery can be accurately obtained without being influenced by the vascular wall.

Note that in a cross-section along the extending direction of the pressure sensor array (a cross-section traversing the artery), an electrode terminal is located in a region that opposes an end portion of the pressure sensor array on the substrate. However, this electrode terminal is located in a region separated from the artery, and therefore is not an obstacle to flattening the outward-facing portion of the vascular wall of the artery.

Also, electrode terminal arrays are not located in the regions that correspond to the two sides of the pressure sensor array on the substrate of the sensor chip. Accordingly, in a cross-section perpendicular to the extending direction of the pressure sensor array (a cross-section substantially along the artery), it is possible to reduce the dimensions of the regions that correspond to the two sides of the pressure sensor array. As a result, it is possible to reduce the pressure force on the measurement site, thus making it possible to reduce pain suffered by the measurement subject. Moreover, the processing circuit that processes output from the pressure sensor elements of the pressure sensor array and transmits the processed output to an electrode terminal of the electrode terminal array is formed in an integrated manner on the substrate, and therefore the need to provide the processing circuit outside of the chip is eliminated, and the circuitry outside the chip is simplified.

In the pulse wave detection apparatus according to an embodiment, the electrode terminal array includes a plurality of electrode terminals arranged side-by-side in a direction perpendicular to the one direction.

In the pulse wave detection apparatus according to the above embodiment, an increase in the dimensions of the sensor chip in the one direction can be suppressed more than in the case where the electrode terminals are arranged side-by-side in the one direction.

In the pulse wave detection apparatus according to an embodiment, the processing circuit is formed in the regions that correspond to the two sides of the pressure sensor array on the substrate.

In the pulse wave detection apparatus according to an embodiment, the processing circuit includes a multiplexer that selects output of the plurality of pressure sensor elements of the pressure sensor array, and retrieves output of a reduced number of pressure sensor elements in a time division manner.

In the pulse wave detection apparatus according to the above embodiment, the processing circuit includes a multiplexer that selects output of the plurality of pressure sensor elements of the pressure sensor array, and retrieves output of a reduced number of pressure sensor elements in a time division manner. This makes it possible to reduce the number of electrode terminals included in the electrode terminal array. Accordingly, it is possible to have a simpler layout for arranging the electrode terminal array on the silicon substrate in the direction perpendicular to the one direction (the lengthwise direction of the sensor chip), and the manufacturing yield is improved. Also, the number of output signals from the pressure sensor elements is reduced, thus simplifying the circuitry outside the chip, and this makes cost reduction possible.

In the pulse wave detection apparatus according to an embodiment, the pulse wave detection apparatus includes a circuit board on which the sensor chip is implemented, and that supports the sensor chip, wherein the electrode terminals of the electrode terminal array of the sensor chip are connected to corresponding electrode pads on the circuit board via wires.

In the pulse wave detection apparatus according to the above embodiment, the electrode terminals of the electrode terminal array of the sensor chip are connected to corresponding electrode pads on the circuit board via wires. These wires are provided by known wire bonding technology, and are provided more precisely than in the case of connection using gold bumps. As a result, the yield in the mounting step is improved.

In the pulse wave detection apparatus according to an embodiment, the wires are sealed with a resin.

In the pulse wave detection apparatus according to the above embodiment, the wires are sealed with a resin. Accordingly, the wires are protected by the resin.

Advantageous Effects of Invention

As is clear from the above description, according to a pulse wave detection apparatus of this invention, it is possible for an outward-facing portion of the vascular wall of an artery to be flattened with good precision, thus making it possible to accurately obtain the internal pressure of a blood vessel.

BRIEF DESCRIPTION OF DRAWINGS

FIG. 6(A) is a cross-sectional view taken along an extending direction of a pressure sensor array, and is for describing the mounted state of the sensor chip. FIG. 6(B) is a cross-sectional view taken along a direction perpendicular to the extending direction of the pressure sensor array, and is for describing the mounted state of the sensor chip.

DESCRIPTION OF EMBODIMENTS

Hereinafter, an embodiment of this invention will be described in detail with reference to the drawings.

Figure 1:
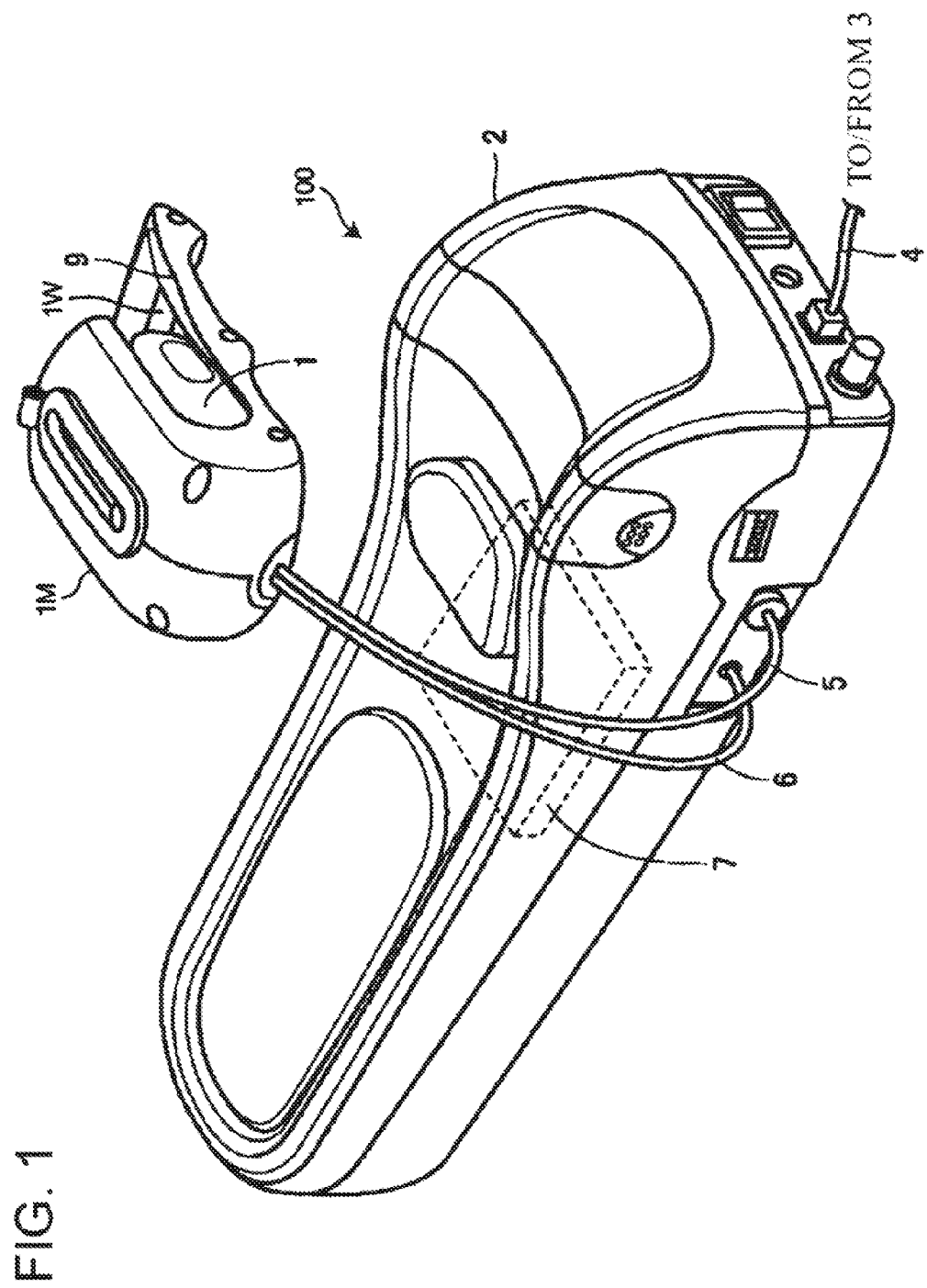
FIG. 1 is a diagram showing a sensor unit and a fixing base that constitute a pulse wave detection apparatus according to an embodiment of this invention.
Figure 2:
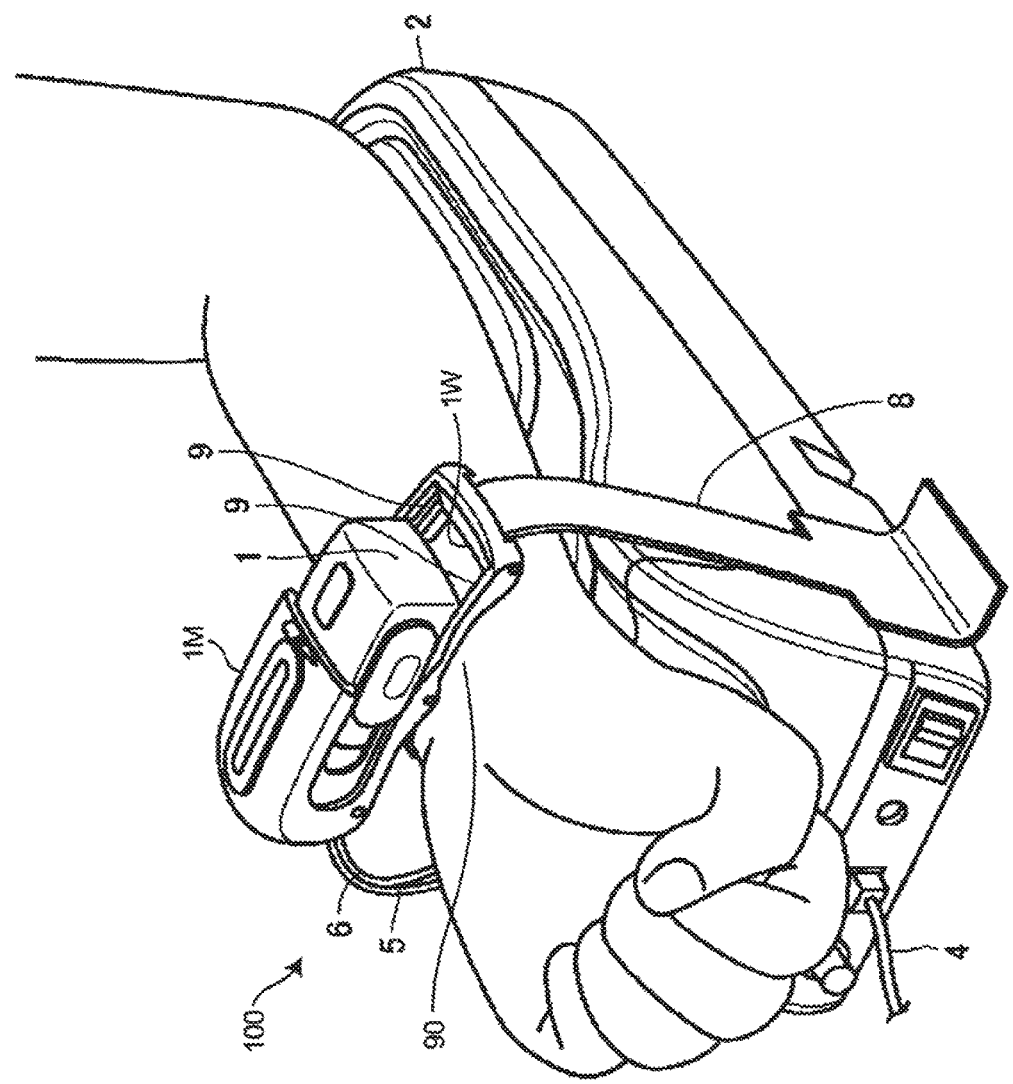
FIG. 2 is a diagram showing a state in which the pulse wave detection apparatus is placed on a measurement site.

FIGS. 1 and 2 show the external appearance of a pulse wave detection apparatus 100 according to an embodiment of this invention. This pulse wave detection apparatus 100 includes a sensor unit 1 that is placed on the surface of a wrist in order to detect a pulse wave in an artery in the wrist, a fixing base 2 for fixing the wrist in order to perform pulse wave detection, and a display unit 3 (see FIG. 9) for the input and output of various types of information related to pulse wave detection. In FIG. 1, the sensor unit 1 is housed in an approximately J-shaped housing 1M, and FIG. 2 shows a state in which the sensor unit 1 has been slid from inside the housing 1M to the outside via sliding grooves 9, and is located above a wrist measurement site (the surface on the palm side, through which radial arteries run) 90, with a window 1W therebetween.

The fixing base 2 includes a fixing base unit 7, and the fixing base unit 7 and the display unit 3 are communicably connected via a USB (Universal Serial Bus) cable 4. Also, the fixing base unit 7 and the sensor unit 1 are connected via a communication cable 5 and an air tube 6.

As shown in FIG. 2, at the time of pulse wave detection, the user places their wrist at a predetermined position on the fixing base 2, the sensor unit 1 is moved to the measurement site 90 of the wrist by sliding movement, and the housing 1M of the sensor unit 1 and the fixing base 2 are tightened via a belt 8, thus preventing the sensor unit 1 from shifting on the wrist.

Figure 3:
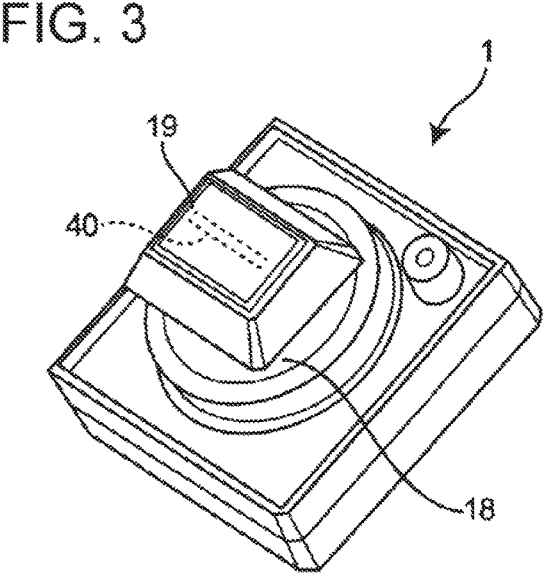
FIG. 3 is a diagram showing a sensor chip provided in the sensor unit.

As shown in FIG. 3, the side of the sensor unit 1 that comes into contact with the wrist (the lower side of the sensor unit 1 in FIGS. 1 and 2) is provided with a sensor chip 19, on which a pressure sensor (strain sensor) array 40 has been formed using MEMS (Micro Electro Mechanical Systems) technology, and a pressure cuff 18 for pressing the sensor chip 19 toward the measurement site 90 of the wrist.

The cuff pressure of the pressure cuff 18 is adjusted by a pressurization pump 15 and a depressurization pump 16 that will be described later, and the sensor chip 19 is moved in a direction of protruding from the sensor unit 1 (or in the opposite direction) by an amount corresponding to the cuff pressure level. Accordingly, the sensor chip 19 protrudes from the window 1W, which was provided in the housing 1M in advance, and is pressed against the measurement site 90.

Figure 5:
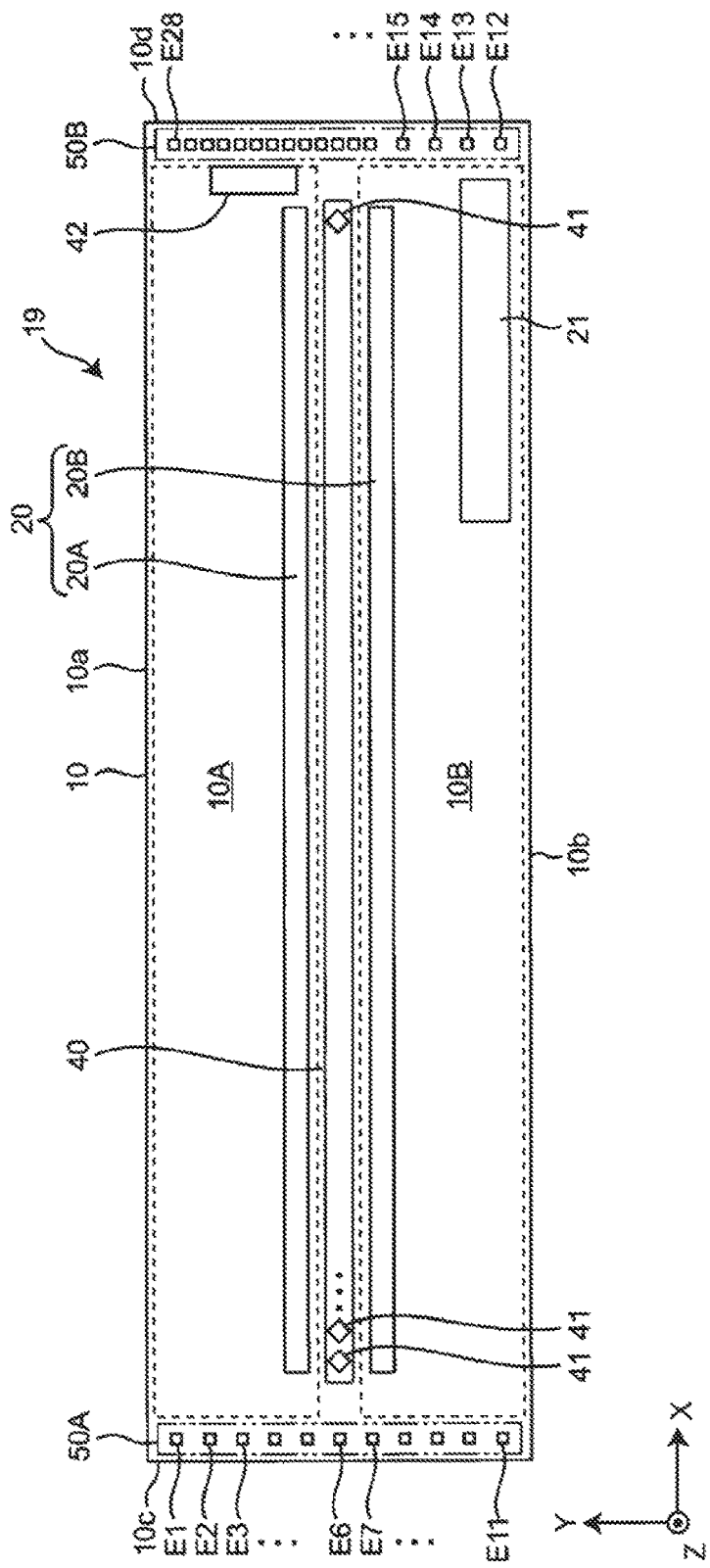
FIG. 5 is a diagram illustratively showing a planar layout of the sensor chip.

FIG. 5 illustratively shows the planar layout of the sensor chip 19. The sensor chip 19 includes a silicon substrate 10 as an approximately flat plate-shaped substrate that is elongated in one direction (X direction), and is configured as an ASIC (Application Specific Integrated Circuit). The X-direction dimension of the silicon substrate 10 is set to approximately 10 mm, the dimension thereof in a Y direction perpendicular to the X direction is set to approximately 3 mm, and the dimension (thickness) thereof in a Z direction perpendicular to the X and Y directions is set to approximately 0.4 mm. The pressure sensor array 40 that extends in the X direction is formed on the silicon substrate 10 at approximately the center in the Y direction. Multiplexers 20A and 20B (collectively indicated by the reference sign 20 when necessary) that extend parallel to the X direction are respectively formed on two sides of the pressure sensor array 40. Electrode terminal arrays 50A and 50B are formed on regions that oppose the end portions of the pressure sensor array 40 on the silicon substrate 10, that is to say, on regions (indicated by dashed double-dotted lines) that extend along short sides 10c and 10d on the two sides in the X direction in this example. A low pass filter (LPF) 42 and an amplifier 21 are formed in the vicinity of the electrode terminal array SOB on the +X side in FIG. 5. Also, interconnects (not shown) for connecting the units 40, 20A, 20B, 42, 21, 50A, and 50B are provided on the silicon substrate 10. Regions 10A and 10B (indicated by dashed lines) that correspond to the two sides of the pressure sensor array 40 in the Y direction are substantially planar surfaces on which electrode terminals do not exist.

The pressure sensor array 40 includes multiple (46 in this example) pressure sensor (strain sensor) elements 41, 41, . . . arranged side-by-side in the X direction with a fixed pitch (a pitch of 0.2 mm in this example). For example, as shown in FIGS. 6(A) and 6(B), the pressure sensor array 40 is formed on a thin region 49 provided by forming a recessed shape in the lower surface side (−Z side) of the silicon substrate 10. The pressure sensor elements 41 are a known type of element that includes a Wheatstone bridge.

Figure 8:
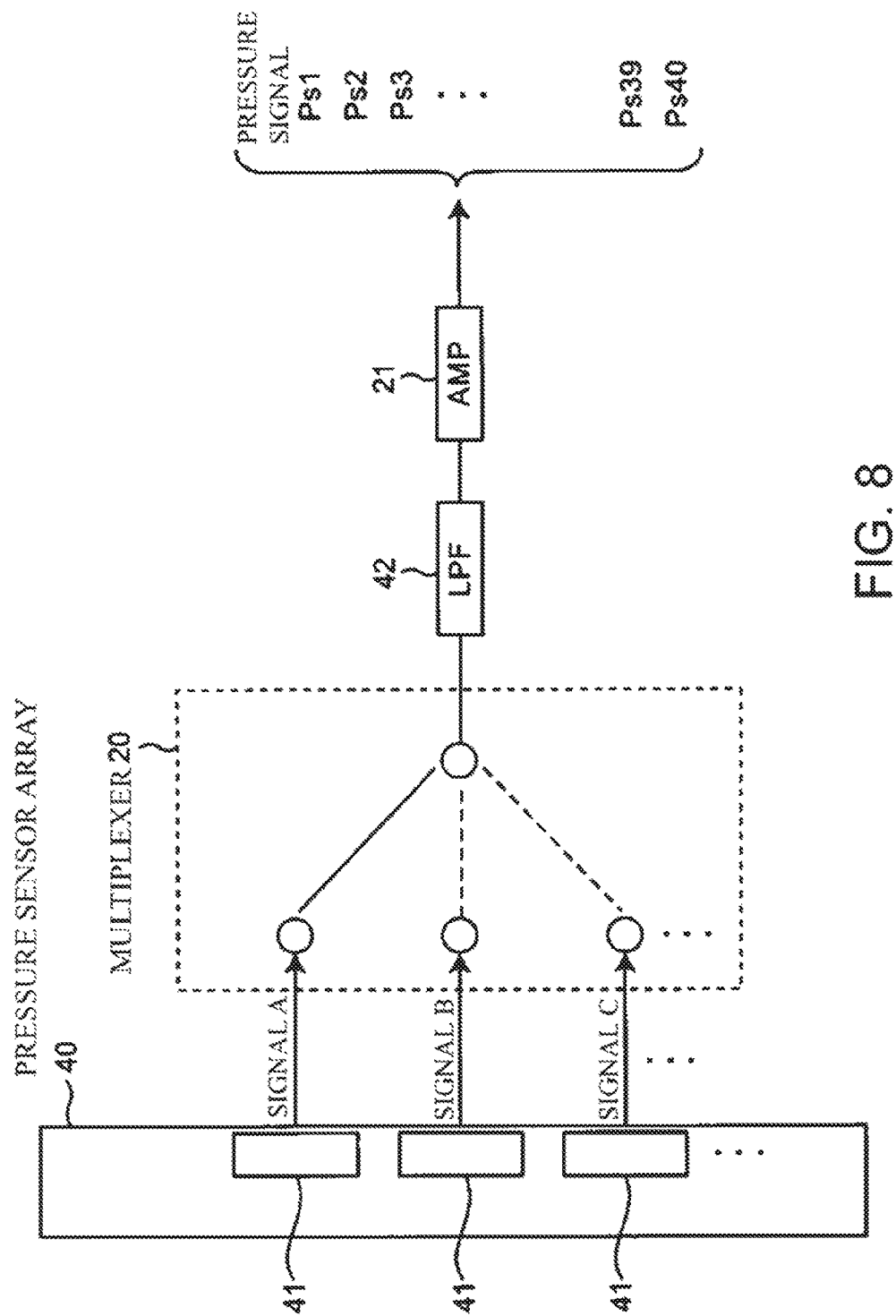
FIG. 8 is a diagram for describing operations of a multiplexer included in the sensor chip.

As shown in FIG. 8, under control of a later-described CPU 11, the multiplexers 20 select output A, B, C, . . . of pressure sensor elements 41, 41, . . . included in the pressure sensor array 40, and retrieve output (pressure signals) Ps1, Ps2, . . . from a reduced number of pressure sensor elements in a time division manner. The number of retrieved pressure signals will be referred to as the "number of channels". In this example, the number of channels is 40 (three pressure sensor elements 41 at each of the two ends of the pressure sensor array 40 are not used).

Note that a configuration is possible in which, for example, every third one of the 46 pressure sensor elements 41, 41, . . . included in the pressure sensor array 40 is used, such that the number of channels is 15 (the one pressure sensor element 41 in each of the end portions of the pressure sensor array is not used). In this case, the pitch of the pressure sensor elements 41, 41 . . . that are used is substantially a pitch of 0.6 mm.

The low pass filter 42 has a cutoff frequency of 500 kHz in this example, removes high-frequency noise that exceeds 500 kHz from the output of the multiplexers 20, and sends the signals at or below 500 kHz to the amplifier 21.

The amplifier 21 amplifies the pressure signals Ps1, Ps2, . . . received from the multiplexers 20 via the low pass filter 42. The amplified pressure signals Ps1, Ps2, . . . are output to the outside of the chip via one of the electrode terminal arrays (the electrode terminal array SOB in FIG. 5 in this example). Note that the amplifier 21 is a chopper amplifier, and therefore a low pass filter (not shown) for reducing noise that accompanies the chopper is included at a stage after the amplifier 21.

As shown in FIG. 5, the electrode terminal array 50A includes electrode terminals E1, E2, . . . , E11 arranged side-by-side in one line in the Y direction. Similarly, the electrode terminal array SOB includes electrode terminals E12, E13, . . . , E28 arranged side-by-side in one line in the Y direction. Arranging the electrode terminals side-by-side in one line in the Y direction in this way suppresses an increase in the X-direction dimension. In this example, the electrode terminals are each a planar aluminum electrode pad with a dimension of approximately 100 μm in the X and Y directions.

For example, the electrode terminal E1 is a terminal that receives, from the later-described CPU 11, a signal for activating (supplying power to) all of the pressure sensor elements 41, 41, . . . (the Wheatstone bridges thereof). The electrode terminal E2 is a terminal for supplying power to the multiplexers 20 and the amplifier 21. The electrode terminal E3 is a terminal to which a ground potential is supplied. The electrode terminals E6 to E11 are terminals that receive, from the CPU 11, signals for controlling operations of the multiplexers 20. The pressure signals that are to be selected and retrieved by the multiplexers 20 from among the output (pressure signals) of the pressure sensor elements 41, 41, . . . are determined by the codes (combinations of high level and low level) of the signals received by the electrode terminals E6 to E11. The electrode terminals E12 and E13 are terminals for outputting, to the outside of the chip, pressure signals Ps1, Ps2, . . . (after amplification by the amplifier 21) that were selected by the multiplexers 20, in a later-described multi-scan mode. The electrode terminals E12 and E13 are terminals also for outputting, to the outside of the chip, a pressure signal of a channel determined to be the optimum channel among the channels, in a later-described fixed channel mode.

As described above, in the sensor chip 19, processing circuits 20, 42, and 21, which are for processing the output of the pressure sensor elements 41 of the pressure sensor array 40 and sending the processed output to the electrode terminals of the electrode terminal array SOB, are formed in an integrated manner on the regions 10A and 10B of the silicon substrate 10 that correspond to the two sides of the pressure sensor array 40. Accordingly, the need to provide these processing circuits outside of the chip is eliminated, and the circuitry outside the chip is simplified.

Also, these processing circuits include the multiplexers 20 that select output of the pressure sensor elements 41 in the pressure sensor array 40 and retrieve output (pressure signals) Ps1, Ps2, . . . of a reduced number of pressure sensor elements 41. This makes it possible to reduce the number of electrode terminals that are included in the electrode terminal arrays 50A and 50B. Accordingly, it is possible to have a simpler layout (the layout in FIG. 5) for arranging the electrode terminal arrays on the silicon substrate 10 in the direction (Y direction) perpendicular to the lengthwise direction (X direction) of the sensor chip 19, and the manufacturing yield is improved. Also, the number of output signals from the pressure sensor elements 41 is reduced, thus simplifying the circuitry outside the chip, and this makes cost reduction possible.

Note that terminals for property testing in the prototype stage of the sensor chip 19 are also included among the electrode terminals in the electrode terminal arrays 50A and S0B whose applications were not described. These property testing terminals can be omitted in the manufacturing stage.

Figure 4:
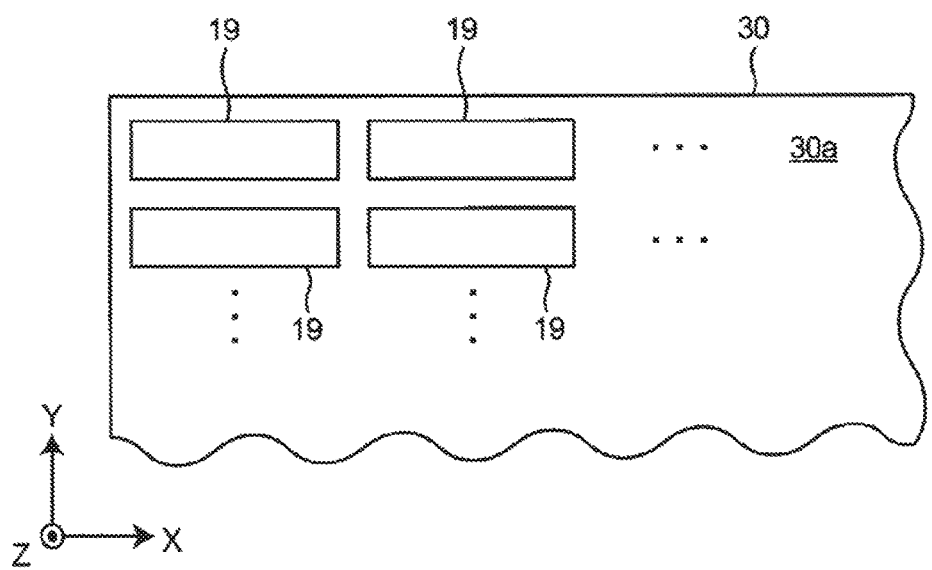
FIG. 4 is a plan view showing how the sensor chip is implemented on a ceramic substrate at the time of mounting.
Figure 7:
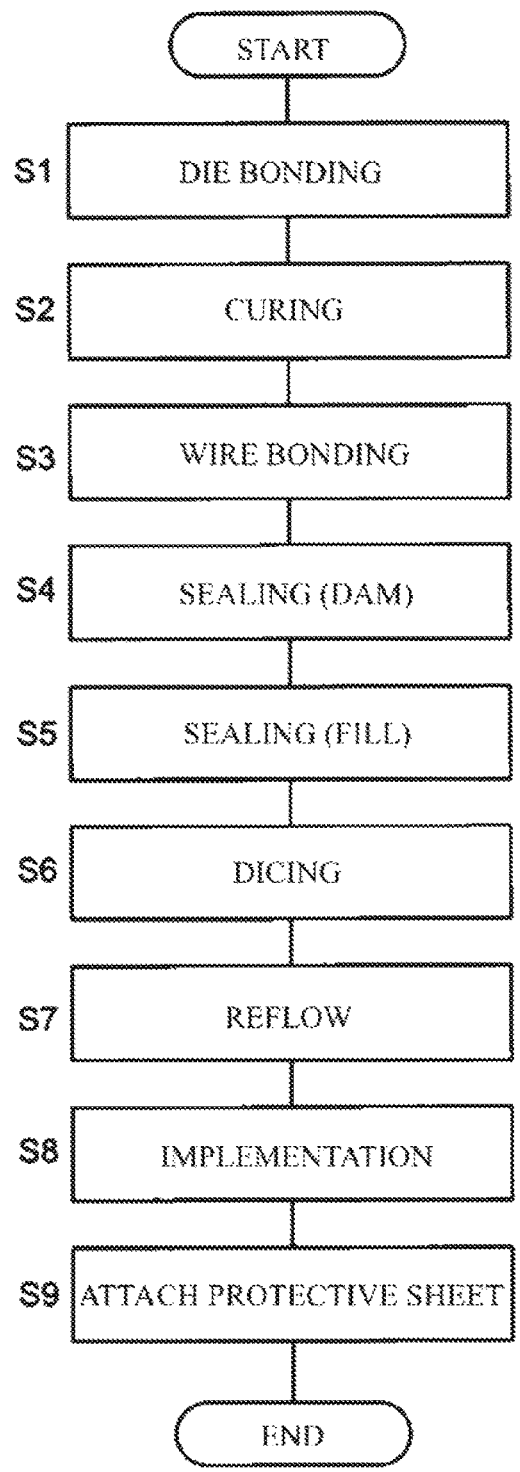
FIG. 7 is a flowchart showing a procedure for mounting the sensor chip.

FIG. 7 shows a procedure for mounting the sensor chip 19.

i) Firstly, as shown in step S1 in FIG. 7, die bond resin (not shown) is used to die bond sensor chips 19, 19, . . . onto an upper surface 30a of a ceramic substrate 30 with a fixed pitch in the X and Y directions as shown in FIG. 4 in this example.

Note that as shown in FIG. 6(A) (a cross-section along the extending direction of the pressure sensor array 40) and FIG. 6(B) (a cross-section perpendicular to the extending direction of the pressure sensor array 40), through-holes 39, which allow the flow of air between the thin region (recessed portion) 49 and the outside, are provided in the ceramic substrate 30 (and a later-described flexible wiring board 31) in correspondence with each of the sensor chips 19 so as to not hinder flexure of the pressure sensor elements 41 in the Z direction.

ii) Next, as shown in step S2 in FIG. 7, curing (heat processing) is performed to harden the die bond resin. Accordingly, the sensor chips 19, 19, . . . are fixed on the ceramic substrate 30.

iii) Next, as shown in FIG. 6(A), pieces of gold wire 32, for example, are used to wire bond the electrode terminals of the electrode terminal arrays 50A and S0B to electrode pads (made up of stacked layers of Au/Cr/Ni in this example) 37 formed on the upper surface 30a of the ceramic substrate 30 (step S3 in FIG. 7). Accordingly, the sensor chips 19 and the ceramic substrate 30 are electrically connected. The pieces of gold wire 32 are provided more precisely than in the case of connection using gold bumps. As a result, the yield in this mounting step is improved.

Note that electrode pads 38 for connection to the later-described flexible wiring board 31 are formed on a lower surface 30b of the ceramic substrate 30. The electrode pads 37 and 38 on the upper surface and the lower surface of the ceramic substrate 30 are electrically connected to each other through via holes (through-holes) that are not illustrated.

iv) Next, as shown in FIG. 6(A), flow prevention resin (dam resin) 33 and 34 are respectively applied along the short sides 10c and 10d on the two sides, with respect to the X direction, of the sensor chips 19, so as to protect the pieces of gold wire 32 (step S4 in FIG. 7). The dam resin 33 is applied on upper surfaces 19a of the sensor chips 19, whereas the dam resin 34 is applied on an upper surface 30a of the ceramic substrate 30. The height of the peak portions of the dam resin 33 and 34 is set so as to slightly exceed the height of the peak portions of the loops of the pieces of gold wire 32.

v) Next, as shown in FIG. 6(A), wire protection resin (fill resin) 35 is applied so as to fill the gaps between the dam resin 33 and 34 and envelop the pieces of gold wire 32 (step S5 in FIG. 7). Accordingly, the pieces of gold wire 32 are enveloped and protected by the fill resin 35.

vi) Next, as shown in FIGS. 6(A) and 6(B), the ceramic substrate 30 is cut along dicing lines DL in the X and Y directions to obtain diced units in which the ceramic substrate 30 and a sensor chip 19 are integrated (step S6 in FIG. 7).

vii) Next, as shown in FIGS. 6(A) and 6(B), reflow (soldering) is performed to electrically connect the electrode pads 38 on the lower surfaces 30b of the individual ceramic substrates 30 to electrode terminals 36 provided on corresponding surfaces 31a of flexible wiring boards (FPCs) 31 (step S7 in FIG. 7). The term "sub assembly" refers to the state in which the flexible wiring board 31 has been attached. Note that a connector 51 for electrical connection with the electrode terminal 36 is provided on a region of the flexible wiring board 31 other than the region on which the ceramic substrate 30 is implemented.

Next, in step S8 in FIG. 7, the sub assembly is implemented on the sensor unit 1 (see FIG. 3). At this time, the connector 51 of the flexible wiring board (FPC) 31 is electrically connected to a corresponding connector (not shown) of the sensor unit 1. In this example, the ceramic substrate 30 and the flexible wiring board (FPC) 31 constitute a circuit board.

Subsequently, in step S9 in FIG. 7, a protective sheet 60 (shown in FIG. 11 for example) is attached so as to cover the sensor unit 1, and cover the sensor chip 19 in particular (mounting completion). In this example, the protective sheet 60 is made up of a silicone resin sheet with a thickness of approximately 150 μm to 300 μm.

Figure 11:
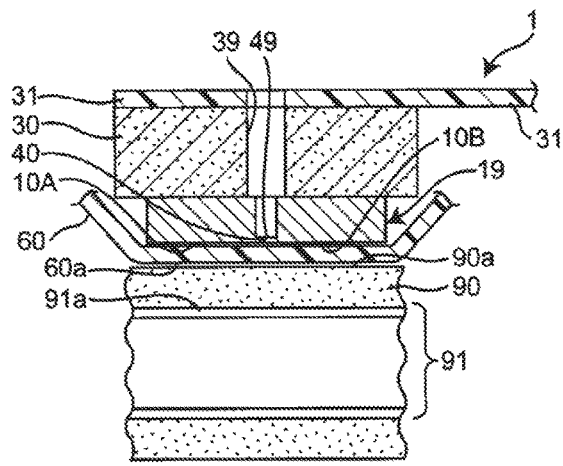
FIG. 11 is a diagram showing a cross-section perpendicular to the extending direction of the pressure sensor array (a cross-section substantially along the artery), in the vicinity of the sensor chip at the time of measurement.
Figure 12:
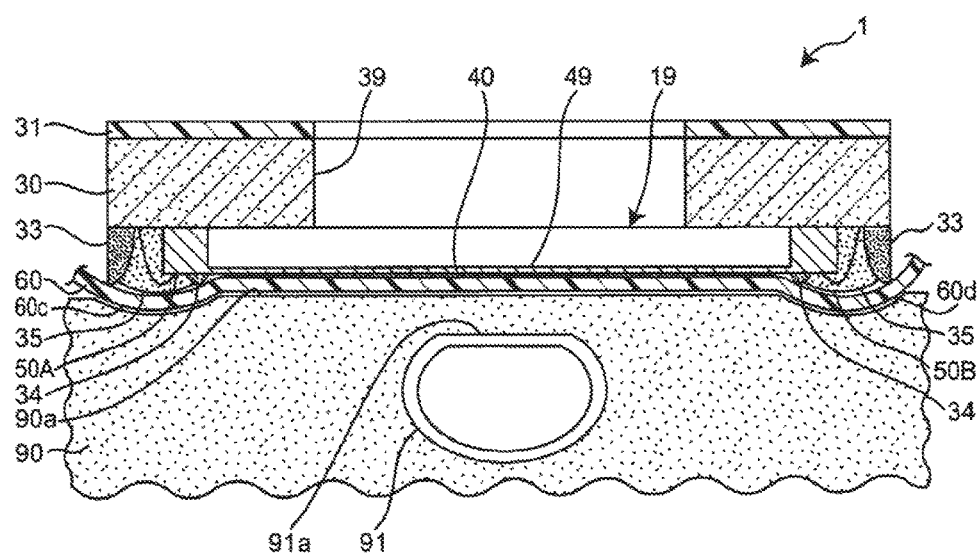
FIG. 12 is a diagram showing a cross-section along the extending direction of the pressure sensor array (a cross-section traversing the artery), in the vicinity of the sensor chip at the time of measurement.

In the mounted state, in a cross-section perpendicular to the extending direction of the pressure sensor array 40 shown in FIG. 1, the regions 10A and 10B of the sensor chip 19 that correspond to the two sides of the pressure sensor array 40 are planar surfaces on which electrode terminals do not exist, and therefore an outer surface 60a of the protective sheet 60 that is pressed against the measurement site 90 is also a planar surface. In a cross-section taken along the extending direction of the pressure sensor array 40 shown in FIG. 12, the electrode terminal arrays 50A and 50B are located on regions of the sensor chip 19 that oppose the end portions of the pressure sensor array 40, and the fill resin 35 and the dam resin 33 and 34 (referred to hereinafter as the "fill resin 35 and the like") in the vicinity of the two sides of the sensor chip 19 bulge in a manner of protruding outward (toward the measurement site 90), and therefore portions 60c and 60d of the protective sheet 60 that correspond to the fill resin 35 and the like also bulge in a manner of protruding outward. As shown in FIGS. 11 and 12, at the time of measurement, the lengthwise direction of the sensor chip 19, that is to say the extending direction of the pressure sensor array 40, is oriented so as to intersect an artery 91.

Figure 9:
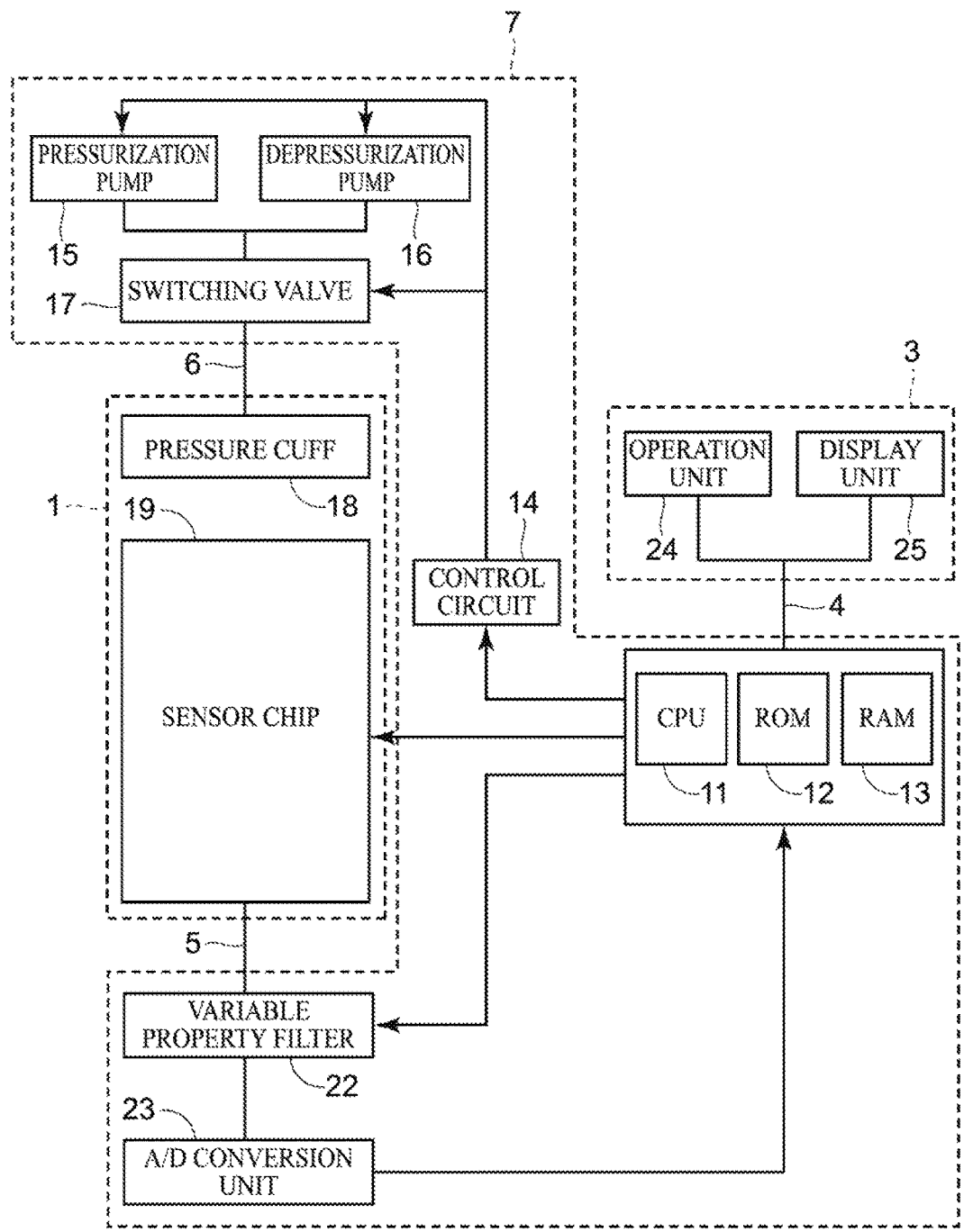
FIG. 9 is a diagram showing a functional block configuration of the pulse wave detection apparatus.

FIG. 9 shows a functional block configuration of the pulse wave detection apparatus 100. The block configuration of the pulse wave detection apparatus 100 is mainly divided into the previously-described sensor unit 1, the fixing base unit 7 included in the fixing base 2, and the display unit 3.

The display unit 3 includes an operation unit 24 that is provided so as to be able to be operated from the outside and is operated in order to input various types of information regarding pulse wave detection, and a display unit 25 constituted by LEDs (Light Emitting Diodes), an LCD (Liquid Crystal Display), or the like for externally outputting various types of information such as artery position detection results and pulse wave measurement results.

The fixing base unit 7 includes a ROM (Read Only Memory) 12 and a RAM (Random Access Memory) 13 that store data and programs for controlling the pulse wave detection apparatus 100; a CPU (Central Processing Unit) 11 that executes various types of processing, including arithmetic operations, in order to perform centralized control of the pulse wave detection apparatus 100; a pressurization pump 15; a depressurization pump 16; a switching valve 17;

a control circuit 14 for receiving control signals from the CPU 11 and controlling the pressurization pump 15, the depressurization pump 16, and the switching valve 17; a variable property filter 22, and an A/D conversion unit 23.

The CPU 11 accesses the ROM 12, reads out a program, deploys it to the RAM 13, and executes it, as well as receives operation signals from the user given using the operation unit 24, and performs overall control of the pulse wave detection apparatus 100 based on the operation signals. In particular, based on operation signals received from the operation unit 24, the CPU 11 transmits, to the control circuit 14, control signals for controlling the pressurization pump 15, the depressurization pump 16, and the switching valve 17. The CPU 11 also causes pulse wave measurement results and the like to be displayed on the display unit 25.

The pressurization pump 15 is a pump for increasing the internal pressure of the pressure cuff (air bag) 18 (referred to hereinafter as the "cuff pressure"), and the depressurization pump 16 is a pump for reducing the cuff pressure. The switching valve 17 selectively connects the air tube 6 to either the pressurization pump 15 or the depressurization pump 16. The control circuit 14 controls the pressurization pump 15, the depressurization pump 16, and the switching valve 17 based on control signals from the CPU 11.

The sensor unit 1 includes the previously-described sensor chip 19 and the pressure cuff 18 that includes an air bag that is pressurized and adjusted so as to press the sensor chip 19 against a wrist.

The variable property filter 22 included in the fixing base unit 7 is a low pass filter for cutting off signal components at or above a cutoff frequency fc. In this example, the variable property filter 22 includes a variable capacitance diode whose capacitance is controlled according to a filter property control voltage from the CPU 11, and can have either of two properties with different cutoff frequencies fc (referred to hereinafter as "property A" and "property B").

Specifically, property A is a state in which the cutoff frequency fc is set to a value fcA that is greater than or equal to a switching frequency fx (20 kHz in this example) that is used when the pressure sensor elements 41, 41, . . . are scanned. The property B is a state in which the cutoff frequency fc is set to a value fcB that is lower than ½ of a sampling frequency fs of the pressure signal from one pressure sensor element. For example, assuming that the switching frequency fx used when scanning the pressure signals Ps1, Ps2, . . . , Ps40 from 40 pressure sensor elements 41, 41, . . . is 20 kHz, the sampling frequency fs of the pressure signal from one pressure sensor element is 500 Hz. In this case, fcA is set to 250 kHz, for example. Also, fcB is set in the range of 30 Hz<fcB<250 Hz (=fs/2), and is set to 100 Hz, for example.

The A/D conversion unit 23 converts pressure signals, which are analog signals, derived from the sensor chip 19 into digital information, and transmits the digital information to the CPU 11. As a result, the CPU 11 can acquire, via the multiplexers 20 in a time division manner, the pressure signals Ps1, Ps2, . . . output by multiple pressure sensor elements 41, 41, . . . included in the sensor chip 19.

Figure 10:
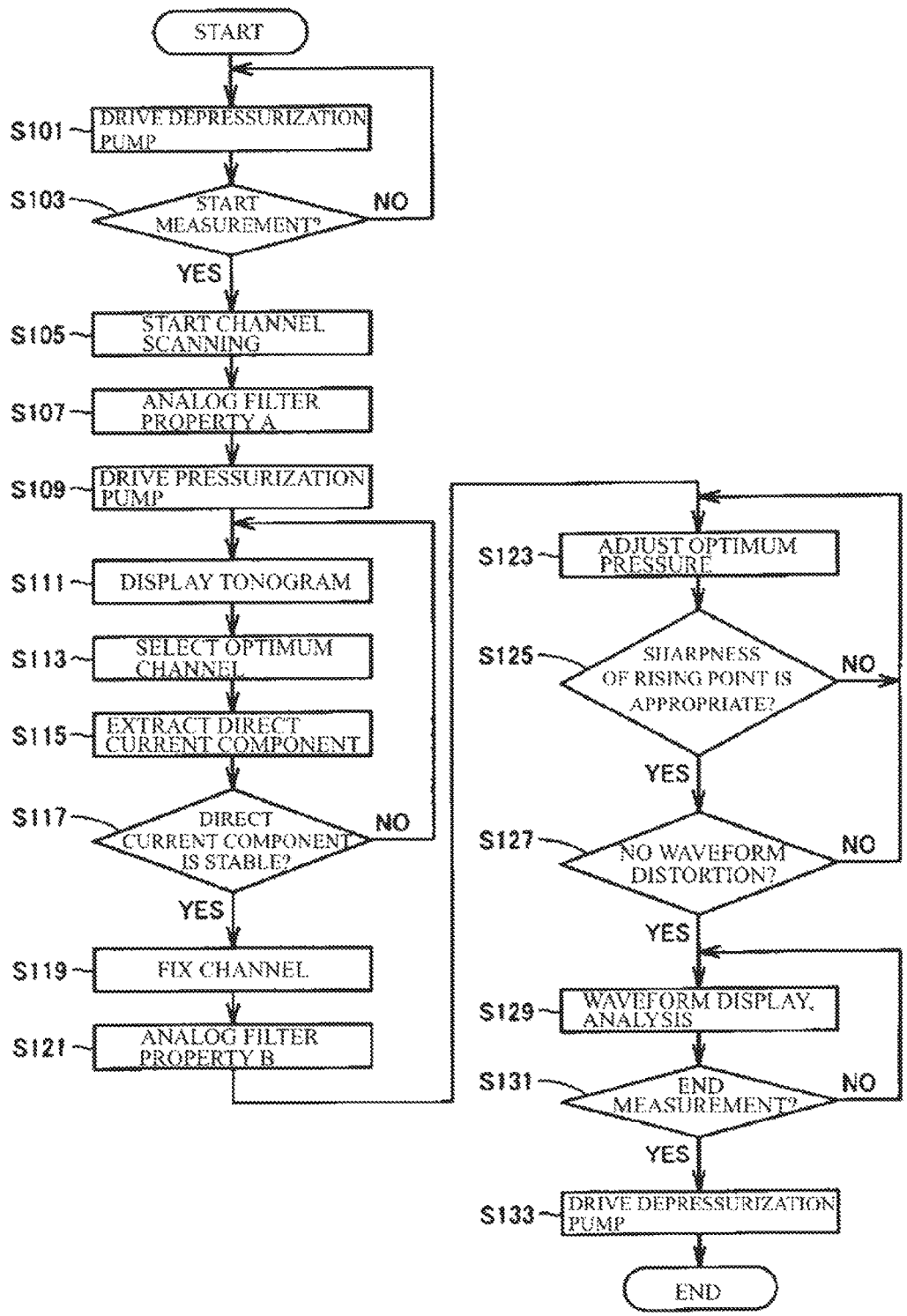
FIG. 10 is a diagram showing a flow of measurement processing performed by the pulse wave detection apparatus.

FIG. 10 shows a flow of measurement processing performed by the pulse wave detection apparatus 100. The measurement processing shown in this flow is realized by the CPU 11 accessing the ROM 12, reading out a program, deploying it to the RAM 13, and then executing it.

Firstly, when a power supply switch (not shown) is switched on, the CPU 11 instructs the control circuit 14 to drive the depressurization pump 16, and then, based on that instruction, the control circuit 14 switches the switching valve 17 to the depressurization pump 16 side and drives the depressurization pump 16 (S101). Due to the depressurization pump 16 being driven, the cuff pressure is set sufficiently lower than atmospheric pressure via the switching valve 17, thus making it possible to avoid a malfunction or failure caused by the sensor chip 19 unexpectedly protruding from the sensor unit 1.

Thereafter, when it is detected that the sensor unit 1 has moved to the measurement site 90, or that a measurement start switch (not shown) included in the operation unit 24 was pressed, or the like, it is determined that measurement is to be started (S103). In the former case, the housing 1M includes a micro switch or the like (not shown) for detecting movement of the sensor unit 1, and the CPU 11 determines whether or not the sensor unit 1 has moved, based on a detection signal from the micro switch.

If it is determined that measurement is to be started (YES in S103), the CPU 11 causes the multiplexers 20 to operate and start channel scanning in order to obtain pressure signals from the pressure sensor elements 41, 41, . . . (S105). This is referred to as the multi-scan mode. In this multi-scan mode, the CPU 11 uses a filter property control signal to switch the variable property filter 22 to the property A and set the cutoff frequency to fcA (S107). Here, fcA is a value greater than or equal to the switching frequency fx of the pressure signals from the pressure sensor elements 41, 41, . . . , thus making it possible to prevent corruption when restoring the waveform.

Next, the CPU 11 transmits a control signal for driving the pressurization pump 15 to the control circuit 14. Based on this control signal, the control circuit 14 switches the switching valve 17 to the pressurization pump 15 side and drives the pressurization pump 15 (S109). Accordingly, the cuff pressure rises, and the sensor chip 19 of the sensor unit 1 is pressed against the surface of the measurement site 90 of the measurement subject.

As shown in FIGS. 11 and 12, at this time, the lengthwise direction of the sensor chip 19, that is to say the extending direction of the pressure sensor array 40, is oriented so as to intersect the artery 91.

When the sensor chip 19 is pressed against the measurement site 90, pressure signals from the pressure sensor elements 41, 41, . . . included in the sensor chip 19 are subjected to time division in the multiplexers 20, then passed through the low pass filter 42, and then amplified in the amplifier 21. Thereafter, the amplified pressure signals are input to the variable property filter 22. The pressure signals that pass through the variable property filter 22 are transmitted to the A/D conversion unit 23. The pressure signals are converted into digital information by the A/D conversion unit 23, and the digital information is input to the CPU 11. The CPU 11 uses the digital information to create a tonogram (a histogram indicating the amplitude of the alternating current component (pulse wave signal) of the pressure signal), and displays the tonogram on the display unit 25 (S111 in FIG. 10)

Figure 13A:
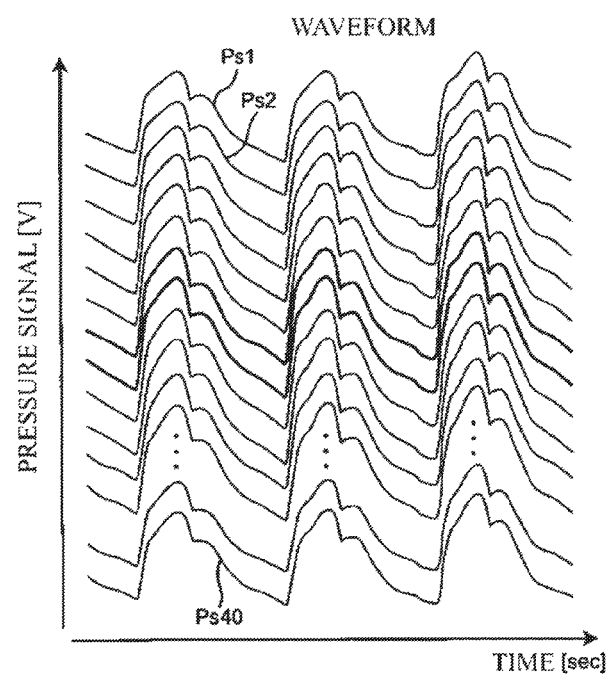
FIG. 13(A) is a diagram showing an example of the waveform of a pressure signal obtained in a multi-scan mode.
Figure 13B:
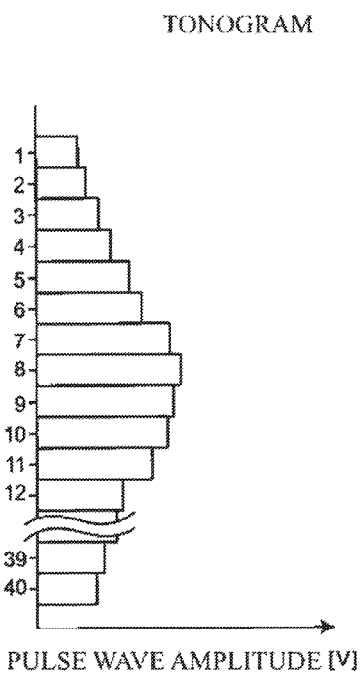
FIG. 13(B) is a diagram showing an example of a tonogram obtained from pressure signals corresponding to multiple channels.

For example, FIG. 13(A) shows the waveforms of pressure signals Ps1, Ps2, . . . , Ps40 corresponding to 40 channels. Note that in order to facilitate understanding in FIG. 13(A), the waveforms of the pressure signals Ps1, Ps2, . . . . Ps40 are drawn so as to be slightly shifted from each other in the vertical direction. As shown in FIG. 13(B), the tonogram is obtained as a histogram indicating the amplitude (pulse wave amplitude) of the alternating current component (pulse wave signal) of the pressure signals Ps1, Ps2, . . . , Ps40. Note that the vertical axis in FIG. 13(B)

indicates the channel numbers that correspond to the pressure signals Ps1, Ps2, . . . , Ps40.

Next, based on the tonogram created in step S111 in FIG. 10, among the pressure sensor elements 41, 41, . . . , the pressure sensor element whose pulse wave amplitude has the highest value (channel 8 in the example in FIG. 13(B)) is detected by the CPU 11 as the pressure sensor element that is located above the artery 91. The CPU 11 then executes processing for selecting the pressure sensor element located above the artery 91 as the optimum channel (S113). Note that known technology such as that disclosed in JP 2004-222847A can be used for the processing for selecting the optimum channel. In this example, it is assumed that one pressure sensor element (indicated by Di) is selected as the optimum channel (note that a configuration is possible in which two or more optimum channels are employed).

Figure 14:
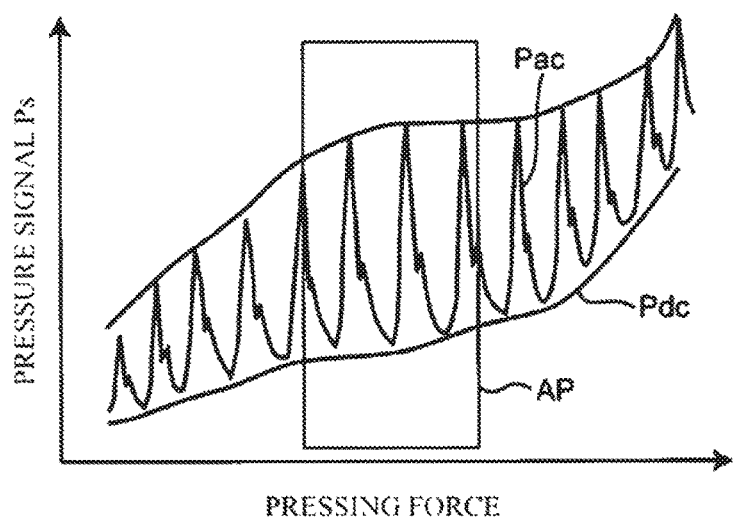
FIG. 14 is a diagram for describing a method for obtaining an optimum pressing force for the sensor chip.

At the same time, the CPU 11 extracts the direct current component from the pressure signals received from the pressure sensor elements 41, 41, . . . , in order to determine the optimum pressing force for the pressure cuff 18 (S115). For example, as shown in FIG. 14, the pressure signal Ps includes a direct current component Pdc and an alternating current component (pulse wave signal) Pac.

The direct current component Pdc is obtained as an average value of the pressure signal in a fixed time period, the component of the pressure signal that has passed through a low pass filter (component obtained after pulse wave removal), or the pressure signal level at the pulse wave rising point (immediately before the pulse wave component becomes mixed in).

More specifically, in step S115 in FIG. 10, the direct current component Pdc can be extracted by dividing change in the pressure signal output into windows (sections) for each fixed time period, and then calculating the average in each window. Alternatively, the direct current component Pdc can be similarly extracted by calculating the median value between the highest value and the lowest value in each window, by extracting the values at or below a predetermined frequency using a low pass filter, or the like. Note that the fixed time period mentioned above is a time interval that has been set in advance in the pulse wave detection apparatus 100 with no relation to the test subject's pulse, and it is preferable that the fixed time period is approximately 1.5 seconds, which includes the general time for one pulse beat.

Next, based on the pressure signals output from the pressure sensor elements 41, 41, . . . , the CPU 11 detects the location where the direct current component Pdc that was extracted in step S115 is stable (S117). If a location where the direct current component Pdc is stable is not detected (NO in S117), the processing of above-described steps S111 to S117 is repeated while continuing to pressurize the pressure cuff 18 with the pressurization pump 15, until a location where the direct current component Pdc is stable is detected.

Then, when the selection of the optimum channel is complete, and a location where the direct current component Pdc is stable is detected (YES in S117), the CPU 11 performs channel fixing such that the multiplexers 20 select the pressure signal from the pressure sensor element Di that was determined to be the optimum channel and transmit the selected pressure signal (S119). This is called the fixed channel mode. In this fixed channel mode, the CPU 11 uses a filter property control signal to switch the variable property filter 22 to the property B and set the cutoff frequency to fcB (e.g., fcB=100 Hz) (S121), fcB is a value lower than ½ of the sampling frequency fs of the pressure signal from one pressure sensor element, and therefore it is possible to remove aliasing noise (i.e., according to the sampling theorem, in the case of converting an analog signal into a digital signal, a noise component having a frequency higher than ½ of the sampling frequency appears in the region lower than ½ of the sampling frequency due to a folding phenomenon). Technology for removing this aliasing noise is disclosed in JP 2005-341994A, for example.

Next, the location where the direct current component Pdc is stable, which was detected in step S117, is temporarily set as the optimum pressing force for the pressure cuff 18, and a control signal is transmitted to the control circuit 14 so as to adjust the pressure of the pressure cuff 18 (S123). For example, in the example in FIG. 14, the optimum pressing force in the range indicated by the box AP is obtained.

Figure 15:
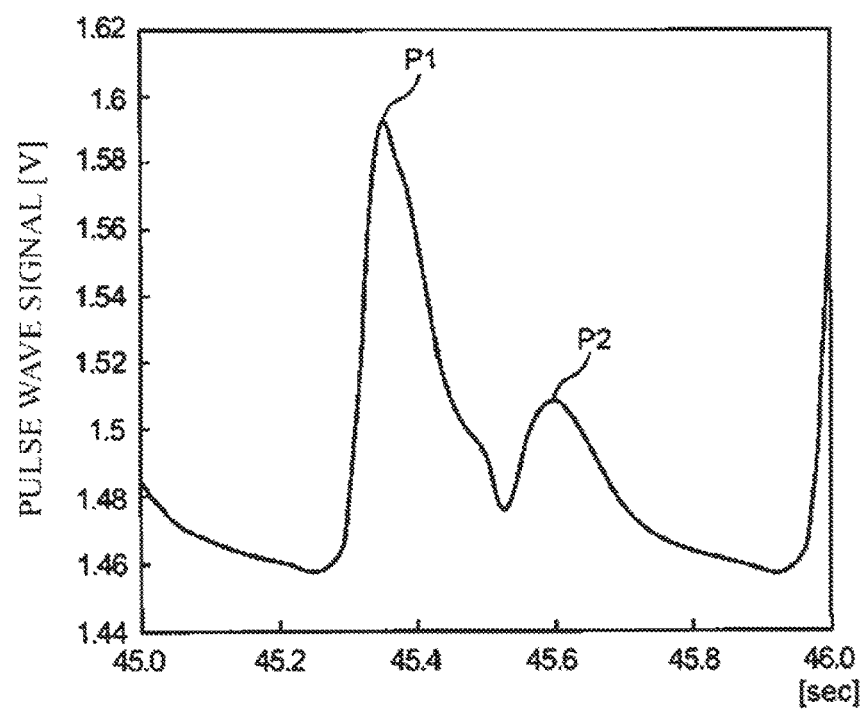
FIG. 15 is a diagram showing an example of the waveform of a pulse wave signal obtained in a fixed channel mode.
Figures 16A, 16B:
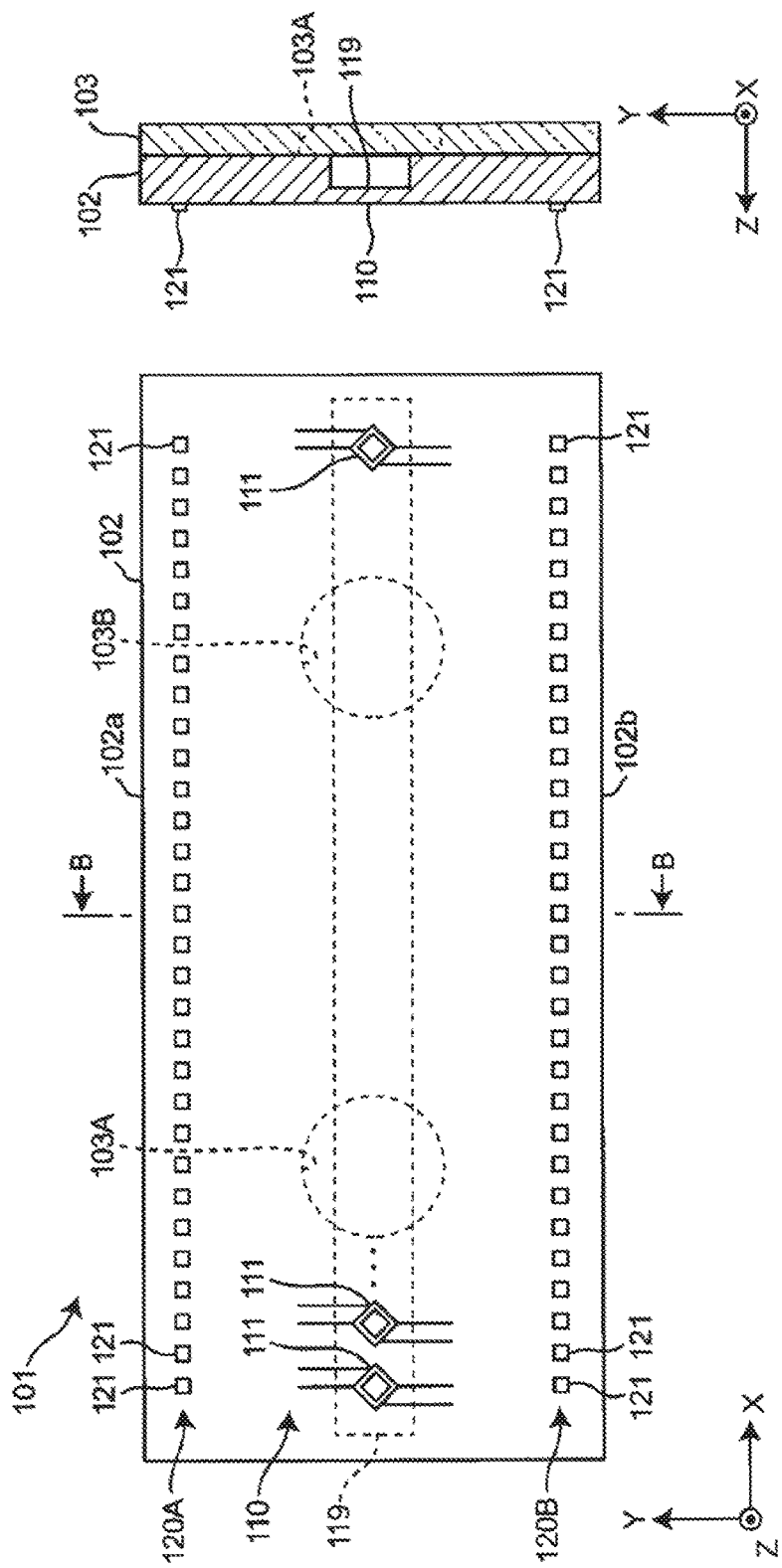
FIG. 16(A) is a diagram illustratively showing the planar layout of a sensor chip included in a conventional commercial product.
FIG. 16(B) is a diagram showing a cross-section taken along line B-B in FIG. 16(A).
Figure 17:
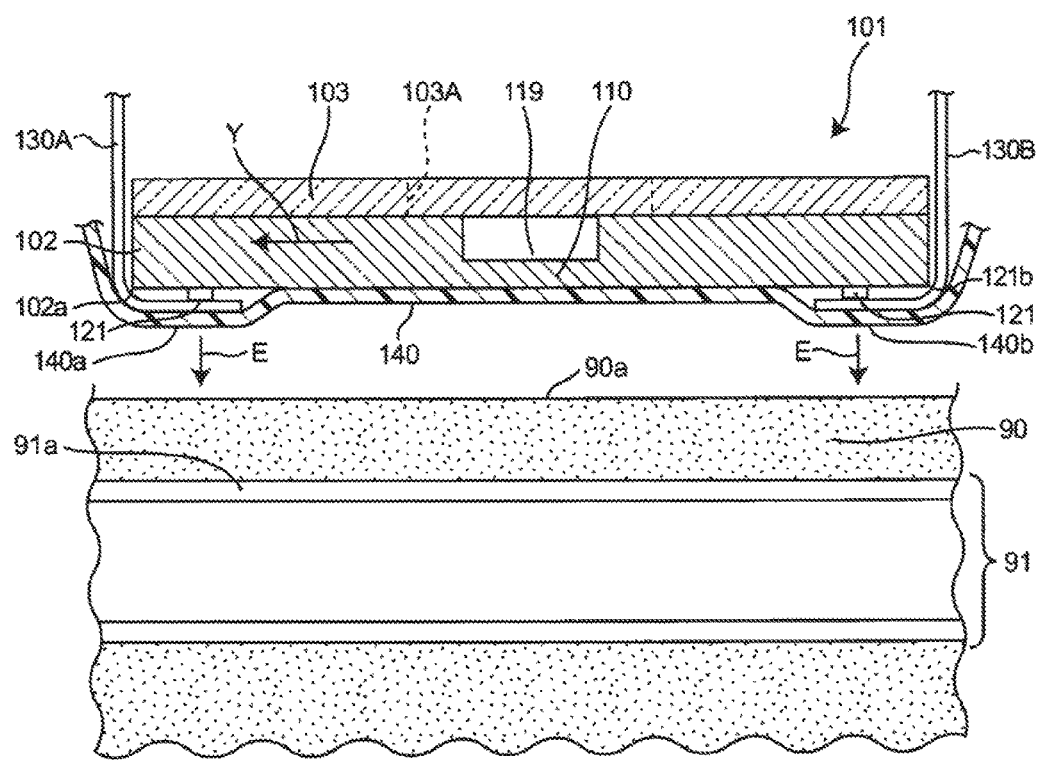
FIG. 17 is a diagram showing a cross-section perpendicular to the extending direction of the pressure sensor array (a cross-section substantially along the artery) in the sensor chip at the time of measurement in a conventional commercial product.
Figure 18:
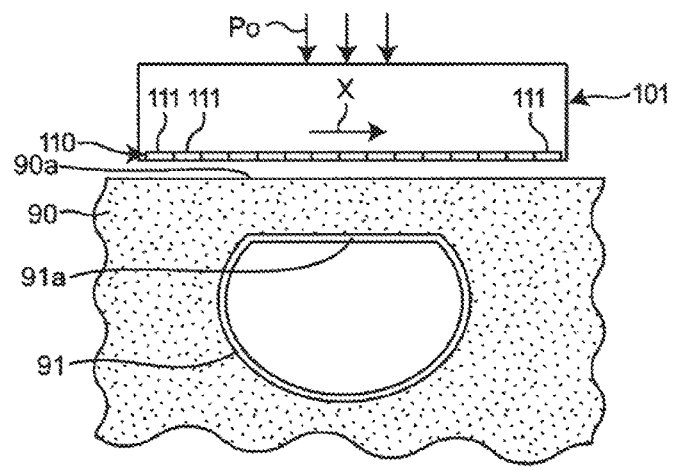
FIG. 18 is a diagram showing a cross-section along the extending direction of the pressure sensor array (a cross-section traversing the artery) in the sensor chip at the time of measurement in the conventional commercial product.
Figure 19A:
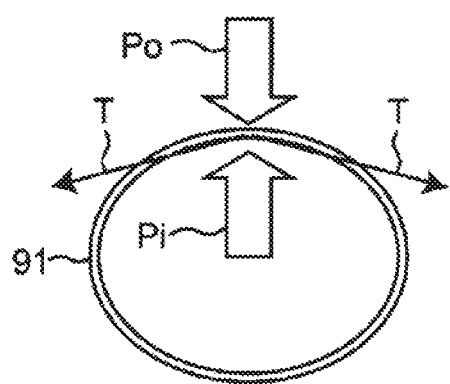
FIG. 19(A) is a diagram illustratively showing the relationship between an external pressure Po and a blood vessel internal pressure Pi in the case where a flattened portion is not formed in an artery.
Figure 19B:
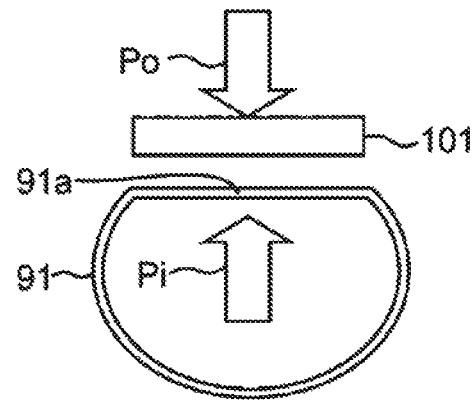
FIG. 19(B) is a diagram illustratively showing the relationship between the external pressure Po and the blood vessel internal pressure Pi in the case where a flattened portion is formed in an artery.

Thereafter, the CPU 11 determines whether or not the pressure signal output from the pressure sensor element Di that was selected as the optimum channel in the state in which the pressing force of the pressure cuff 18 is maintained at the optimum pressure (i.e., the sharpness (MSP) of the rising point in the waveform data illustrated in FIG. 15) is appropriate (S125), and furthermore determines whether or not waveform distortion exists (S127). Note that in FIG. 15, P1 indicates the peak of the ejected wave, and P2 indicates the peak of the reflected wave.

If the sharpness (MSP) of the rising point in the waveform data is not appropriate (NO in S125 in FIG. 10), or if waveform distortion is detected (NO in S127), pressing force adjustment in step S123 is repeated until the sharpness of the rising point in the waveform data becomes appropriate, or until waveform distortion is no longer detected.

Then, in the case where the sharpness (MSP) of the rising point in the waveform data is appropriate (YES in S125), and waveform distortion is not detected (YES in S127), the CPU 11 acquires the waveform data at that point in time via the multiplexers 20, the amplifier 21, the variable property filter 22, and the A/D conversion unit 23 (S129).

Thereafter, the CPU 11 detects a pulse wave based on the acquired waveform data, and determines that a predetermined condition for ending pulse wave detection has been established (S131). The condition for ending pulse wave detection in step S131 may be that a predetermined time period (e.g., 30 seconds) that was set in advance has elapsed, or may be an end (or interrupt) instruction from the user, or the like. In other words, the pulse wave data transfer processing in step S129 described above is repeated until the predetermined condition is established.

When the predetermined condition for ending pulse wave detection has been established (YES in S131), the CPU 11 transmits a control signal to the control circuit 14 so as to drive the depressurization pump 16 via the switching valve 17 (S133). Accordingly, the state of pressing the sensor chip 19 against the measurement site 90 is released, and the series of pulse wave measurement processing ends.

In this way, in the case where pulse wave measurement is performed, in a cross-section perpendicular to the extending direction of the pressure sensor array 40 (a cross-section along the artery 91) shown in FIG. 11, the regions 10A and 10B of the sensor chip 19 that correspond to the two sides of the pressure sensor array 40 are planar surfaces on which electrode terminals do not exist, and therefore the outer surface 60a of the protective sheet 60 that is pressed against the measurement site 90 is also a planar surface. Accordingly, there are no obstacles to flattening the outward-facing portion 91a of the vascular wall of the artery 91. As a result, the outward-facing portion 91a of the vascular wall of the artery 91 can be flattened with good precision. Accordingly, change in the internal pressure of the artery 91 can be accurately obtained without being influenced by the vascular wall.

Note that in a cross-section taken along the extending direction of the pressure sensor array 40 (a cross-section traversing the artery 91) shown in FIG. 12, the electrode terminal arrays 50A and 50B are located on regions of the sensor chip 19 that oppose the end portions of the pressure sensor array 40, and the fill resin 35 and the like in the vicinity of the two sides of the sensor chip 19 bulge in a manner of protruding outward (toward the measurement site 90). However, the electrode terminal arrays 50A and 50B and the fill resin 35 and the like are located in regions separated from the artery 91, and therefore are not obstacles to flattening the outward-facing portion 91a of the vascular wall of the artery 91.

Also, as shown in FIG. 11, electrode terminal arrays are not located in the regions 10A and 11B on the silicon substrate 10 of the sensor chip 19 that correspond to the two sides of the pressure sensor array 40, and therefore it is possible to reduce the dimensions of the regions 10A and 10B that correspond to the two sides of the pressure sensor array 40. In this case, the processing circuit in the sensor chip 19 may be simplified by providing the low pass filter 42 and the amplifier 21 outside the chip, for example. As a result, it is possible to reduce the pressure force on the measurement site 90, thus making it possible to reduce pain suffered by the measurement subject.

Although the silicon substrate 10 is used as the substrate that forms the sensor chip 19 in this embodiment, there is no limitation to this. The substrate need only be able to have a pressure sensor (strain sensor) array formed thereon by MEMS technology, and may be a substrate made of another material.

Also, although the ceramic substrate 30 and the flexible wiring board 31 are used as circuit boards in this embodiment, there is no limitation to this. The circuit boards need only be able to support the aforementioned substrates and be provided with interconnects for connection with electrode terminals on the substrates, and may be substrates made of another material. For example, a configuration is possible in which a portion of the flexible wiring board 31 is given a rigid configuration, and the sensor chip 19 is implemented directly on the rigid portion.

Also, although the protective sheet 60 is provided so as to cover the sensor chip 19 in this embodiment, there is no limitation to this. The pieces of gold wire 32 and the upper surface of the sensor chip 19 may be provided with a substantially flat coating of resin so as to be sealed and protected.

Also, although the electrode terminals included in the electrode terminal arrays 50A and S0B are arranged side-by-side in one line in the Y direction, there is no limitation to this. The electrode terminal arrays 50A and 50B need only be provided on regions that oppose the end portions of the pressure sensor array 40. For example, the electrode terminal arrays 50A and 50B may each have an arrangement of two lines in the Y direction that are shifted from each other by ½ pitch (so-called staggered arrangement). This case makes it possible to reduce the Y-direction dimension of the sensor chip 19 more than in the case of one line.

The above-described embodiment is merely an example and can be modified in various ways without departing from the scope of the invention. The above-described embodiments can be realized independently of each other, and embodiments can also be combined. Various characteristics of different embodiments can also be realized independently of each other, and characteristics of different embodiments can also be combined.

REFERENCE SIGNS LIST

1 Sensor unit
1M Housing
2 Fixing base
8 Belt
9 Sliding groove
18 Pressure cuff
19 Sensor chip
20, 20A, 20B Multiplexer
21 Amplifier
22 Variable property filter
40 Pressure sensor array
41 Pressure sensor element
42 Low pass filter
50A, 50B Electrode terminal array
E1, E2, . . . , E28 Electrode terminal

The invention claimed is:

1. A pulse wave detection apparatus that detects a pulse wave in a noninvasive manner by pressing a sensor chip having a pressure sensor array formed thereon against a measurement site through which an artery passes, the apparatus comprising:
   the sensor chip comprising:
      a substrate that has a shape of extending so as to be elongated in one direction, and that is arranged so as to intersect the artery;
      a pressure sensor array that is formed on the substrate and is made up of a plurality of pressure sensor elements arranged side-by-side in the one direction;
      an electrode terminal array for transmitting output from the plurality of pressure sensor elements to outside of the sensor chip, the electrode terminal array being formed in a region that opposes an end portion of the pressure sensor array on the substrate, regions that correspond to two sides of the pressure sensor array on the substrate are planar surfaces on which electrode terminals are not located; and
      a processing circuit formed in an integrated manner on the substrate, the processing circuit processing output from the pressure sensor elements of the pressure sensor array and transmitting the processed output to an electrode terminal of the electrode terminal array, the processing circuit including a multiplexer that extends parallel to the pressure sensor array.

2. The pulse wave detection apparatus according to claim 1, wherein the electrode terminal array includes a plurality of electrode terminals arranged side-by-side in a direction perpendicular to the one direction.

3. The pulse wave detection apparatus according to claim 2, wherein the processing circuit is formed in the regions that correspond to the two sides of the pressure sensor array on the substrate.

4. The pulse wave detection apparatus according to claim 3, wherein the multiplexer selects output of the plurality of pressure sensor elements of the pressure sensor array, and retrieves output of a reduced number of pressure sensor elements in a time division manner.

5. The pulse wave detection apparatus according to claim 4, further comprising:
   a circuit board on which the sensor chip is implemented, and that supports the sensor chip, wherein the electrode terminals of the electrode terminal array of the sensor chip are connected to corresponding electrode pads on the circuit board via wires.

6. The pulse wave detection apparatus according to claim 5, wherein the wires are sealed with a resin.

7. The pulse wave detection apparatus according to claim 3, further comprising:
a circuit board on which the sensor chip is implemented, and that supports the sensor chip,
wherein the electrode terminals of the electrode terminal array of the sensor chip are connected to corresponding electrode pads on the circuit board via wires.

8. The pulse wave detection apparatus according to claim 7, wherein the wires are sealed with a resin.

9. The pulse wave detection apparatus according to claim 2, further comprising:
a circuit board on which the sensor chip is implemented, and that supports the sensor chip,
wherein the electrode terminals of the electrode terminal array of the sensor chip are connected to corresponding electrode pads on the circuit board via wires.

10. The pulse wave detection apparatus according to claim 9, wherein the wires are sealed with a resin.

11. The pulse wave detection apparatus according to claim 1, wherein the processing circuit is formed in the regions that correspond to the two sides of the pressure sensor array on the substrate.

12. The pulse wave detection apparatus according to claim 11, wherein the multiplexer selects output of the plurality of pressure sensor elements of the pressure sensor array, and retrieves output of a reduced number of pressure sensor elements in a time division manner.

13. The pulse wave detection apparatus according to claim 12, further comprising:
a circuit board on which the sensor chip is implemented, and that supports the sensor chip,
wherein the electrode terminals of the electrode terminal array of the sensor chip are connected to corresponding electrode pads on the circuit board via wires.

14. The pulse wave detection apparatus according to claim 13, wherein the wires are sealed with a resin.

15. The pulse wave detection apparatus according to claim 11, further comprising:
a circuit board on which the sensor chip is implemented, and that supports the sensor chip,
wherein the electrode terminals of the electrode terminal array of the sensor chip are connected to corresponding electrode pads on the circuit board via wires.

16. The pulse wave detection apparatus according to claim 15, wherein the wires are sealed with a resin.

17. The pulse wave detection apparatus according to claim 1, further comprising:
a circuit board on which the sensor chip is implemented, and that supports the sensor chip,
wherein the electrode terminals of the electrode terminal array of the sensor chip are connected to corresponding electrode pads on the circuit board via wires.

18. The pulse wave detection apparatus according to claim 17, wherein the wires are sealed with a resin.

* * * * *